US00PP37130P2

(12) United States Plant Patent
Beers

(10) Patent No.: US PP37,130 P2
(45) Date of Patent: Dec. 9, 2025

(54) ***DIANTHUS* PLANT NAMED 'Hilpicperf'**

(50) Latin Name: ***Dianthus caryophyllus* L.**
Varietal Denomination: Hilpicperf

(71) Applicant: HilverdaFlorist B.V., De Kwakel (NL)

(72) Inventor: Martin Beers, Hoofddorp (NL)

(73) Assignee: HILVERDA FLORIST B.V., De Kwakel (NL)

( * ) Notice: Subject to any disclaimer, the term of this patent is extended or adjusted under 35 U.S.C. 154(b) by 0 days.

(21) Appl. No.: 18/814,504

(22) Filed: Aug. 24, 2024

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./273
See application file for complete search history.

(56) References Cited

PUBLICATIONS https://www.floraldaily.com/article/9635891/hilverdaflorist-launches-dianthus-picture-perfect-branding-concept-at-flowertrials-2024/ Retrieved from the Internet on Apr. 23, 2025.*
https://www.hortinno.com/news/flowertrialsr-2024-what-it-when-where Retrieved from the Internet on Apr. 23, 2025.*
https://plantariumgroendirekt.nl/nieuwigheden-en/?lang=en Retrieved on Apr. 23, 2025.*

* cited by examiner

*Primary Examiner* — Susan Mccormick Ewoldt
(74) *Attorney, Agent, or Firm* — C. Anne Whealy

(57) ABSTRACT

A new and distinct cultivar of *Dianthus* plant named 'Hilpicperf', characterized by its compact, upright to outwardly spreading and uniformly mounding plant habit; freely branching habit; relatively broad dark green-colored leaves; early and freely flowering habit; relatively long flowering period; purplish red and dark red bi-colored semi-double-type flowers; and good container and garden performance.

1 Drawing Sheet

Cultivar denomination: 'HILPICPERF'.
Botanical classification: *Dianthus caryophyllus* L.

CROSS-REFERENCED TO CLOSELY-RELATED APPLICATION

A European Community Plant Breeder's Rights application for the instant plant was filed by the Applicant/Assignee of the instant application, HilverdaFlorist B.V. of De Kwakel, The Netherlands on Jul. 11, 2024, application number 2024/1640. Foreign priority is not claimed to this European Community Plant Breeder's Rights application.

BACKGROUND OF THE INVENTION

The present invention relates to a new and distinct cultivar of *Dianthus* plant, botanically known as *Dianthus caryophyllus* L., grown commercially as a container and garden plant and hereinafter referred to by the name 'Hilpicperf'.

The new *Dianthus* plant is a product of a planned breeding program conducted by the Inventor in De Kwakel, The Netherlands. The objective of the breeding program is to create new *Dianthus* plants with numerous attractive flowers and good container and garden performance.

The new *Dianthus* plant originated from a cross-pollination made by the Inventor in De Kwakel, The Netherlands in May 2017 of a proprietary selection of *Dianthus caryophyllus* L. identified as code number 6045, not patented, as the female, or seed, parent with a proprietary selection of *Dianthus caryophyllus* L. identified as code number 1679, not patented, as the male, or pollen, parent. The new *Dianthus* plant was discovered and selected by the Inventor as a single flowering plant from within the progeny of the stated cross-pollination in a controlled greenhouse environment in De Kwakel, The Netherlands in June 2018.

Asexual reproduction of the new *Dianthus* plant by terminal cuttings propagated in a controlled greenhouse environment in De Kwakel, The Netherlands since June 2018 has shown that the unique features of this new *Dianthus* plant are stable and reproduced true to type in successive generations of asexual reproduction.

SUMMARY OF THE INVENTION

Plants of the new *Dianthus* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilpicperf'. These characteristics in combination distinguish 'Hilpicperf' as a new and distinct *Dianthus* plant:

1. Compact, upright to outwardly spreading and uniformly mounding plant habit.
2. Freely branching habit.
3. Relatively broad dark green-colored leaves.
4. Early and freely flowering habit.
5. Relatively long flowering period.
6. Purplish red and dark red bi-colored semi-double-type flowers.
7. Good container and garden performance.

In side-by-side comparisons, plants of the new *Dianthus* differ primarily from plants of the female parent selection in the following characteristics:

1. Leaves of plants of the new *Dianthus* are broader than leaves of plants of the female parent selection.
2. Leaves of plants of the new *Dianthus* are darker green in color than leaves of plants of the female parent selection.

In side-by-side comparisons, plants of the new *Dianthus* differ primarily from plants of the male parent selection in the following characteristics:

1. Plants of the new *Dianthus* have slightly lighter green-colored leaves than plants of the male parent selection.
2. Plants of the new *Dianthus* flower earlier than plants of the male parent selection.

Plants of the new *Dianthus* also can be compared to plants of *Dianthus caryophyllus* 'Kobianca', disclosed in U.S. Plant Pat. No. 19,751. In side-by-side comparisons, plants of the new *Dianthus* differ primarily from plants of 'Kobianca' in the following characteristics:

1. Plants of the new *Dianthus* are more compact than plants of 'Kobianca'.
2. Flowers of plants of the new *Dianthus* are semi-double-types whereas flowers of plants of 'Kobianca' are double- types.
3. Flowers of plants of the new *Dianthus* are purplish red and dark red bi-colored whereas flowers of plants of 'Kobianca' are red purple and white bi-colored.

BRIEF DESCRIPTION OF THE PHOTOGRAPH

The accompanying photograph illustrates the overall appearance of the new *Dianthus* plant showing the colors as true as it is reasonably possible to obtain in colored reproductions of this type. Colors in the photograph may differ slightly from the color values cited in the detailed botanical description which accurately describe the colors of the new *Dianthus* plant.

The photograph is a side perspective view of a typical flowering plant of 'Hilpicperf' grown in a container.

DETAILED BOTANICAL DESCRIPTION

Plants used in the aforementioned photograph and following observations and measurements were grown during the spring in 10-cm containers in a glass-covered greenhouse in De Kwakel, The Netherlands and under cultural practices typical of commercial container *Dianthus* production. During the production of the plants, day temperatures ranged from 16° C. to 20° C. and night temperatures ranged from 16° C. to 18° C. Plants used for the photograph and description were three months from planting and were pinched one time about five weeks after planting rooted young plants. In the following description, color references are made to The Royal Horticultural Society Colour Chart, 2015 Edition, except where general terms of ordinary dictionary significance are used.

Botanical classification: *Dianthus caryophyllus* L. 'Hilpicperf'.

Parentage:

*Female, or seed, parent.*—Proprietary selection of *Dianthus caryophyllus* L. identified as code number 6045, not patented.

*Male, or pollen, parent.*—Proprietary selection of *Dianthus caryophyllus* L. identified as code number 1679, not patented.

Propagation:

*Type.*—By terminal vegetative cuttings.

*Time to initiate roots, summer.*—About six days at temperatures ranging from 20° C. to 25C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Herbaceous perennial, typically grown as a container and garden plant; compact, upright to outwardly spreading and uniformly mounding plant habit; moderately vigorous growth habit; slow to moderate growth rate; flowers held above the foliar plane.

*Plant height, soil level to top of foliar plane.*—About 11.6 cm.

*Plant height, soil level to top of floral plane.*—About 15 cm.

*Plant diameter or spread.*—About 22.3 cm.

*Lateral branches.*—Branching habit: Freely branching habit with about eight main (basal) stems; each main stem with about three to seven lateral branches; pinching is not required, however, pinching will enhance lateral branch development. Length: About 10.6 cm. Diameter: About 2 mm. Internode length: About 3.1 cm. Strength: Strong. Aspect: About 30° from vertical. Texture and luster: Smooth, glabrous; glossy overlain with a thin waxy layer which is matte. Color, developing: Close to 145C. Color, developed: Close to 137A; waxy layer, close to 190C.

Leaf description:

*Arrangement.*—Opposite, simple; sessile.

*Length.*—About 6.5 cm.

*Width.*—About 5 mm.

*Shape.*—Narrowly oblanceolate; slightly carinate.

*Apex.*—Acute.

*Base.*—Attenuate; decurrent.

*Margin.*—Entire; not lobed.

*Texture and luster, upper surface.*—Smooth, glabrous; matte.

*Texture and luster, lower surface.*—Smooth, glabrous; slightly glossy overlain with a thin waxy later which is matte.

*Venation pattern.*—Parallel; only midvein is discernible.

*Color.*—Developing leaves, upper surface: Close to 143C. Developing leaves, lower surface: Close to 143C; waxy layer, close to 138B. Fully expanded leaves, upper surface: Close to 147A; venation, close to 147A. Fully expanded leaves, lower surface: Close to NN137A to NN137B; waxy layer, close to 138B; venation, close to NN137A to NN137B.

Flower description:

*Flower form and flowering habit.*—Rotate semi-double-type flowers arranged singly or in pairs; freely flowering habit with about 70 flower buds and open flowers per plant at one time; flowers face mostly upright to slightly outwardly.

*Natural flowering season.*—Flowering is continuous for about 16 weeks during the spring to late summer in The Netherlands.

*Postproduction longevity.*—Flowers last about ten days on the plant; flowers not persistent.

*Fragrance.*—Faintly fragrant; clove-like, sweet and pleasant.

*Flower buds.*—Length: About 1.8 cm. Diameter: About 5 mm. Shape: Oblong. Texture and luster: Smooth, glabrous; slightly glossy. Color: Close to 138A; towards the base, close to 144C; towards the apex, immature petals, close to 71D.

*Flower diameter.*—About 2.7 cm by 2.7 cm.

*Flower depth.*—About 3.3 cm.

*Petals.*—Quantity and arrangement: Five petals arranged in a single whorl. Length: About 3.5 cm. Width: About 1.9 cm. Shape: Spatulate. Apex: Praemorse to narrowly emarginate. Base: Narrowly cuneate to close to acuminate. Margin: Distally, irregularly and finely dentate; proximally, entire; not undulate. Texture and luster, upper surface: Smooth, glabrous; velvety; matte. Texture and luster, lower surface: Smooth, glabrous; velvety; slightly glossy. Color: When opening, upper surface: Close to a blend of 187C and 187D; distal 25% of the petal, close to N74B; towards the base, close to NN155D and at the base, close to 149D. When opening, lower surface: Close to 196D; distal 25% of the petal, close to 73B; towards the base, close to NN155C and at the base, close to 149D. Fully developed, upper surface: Close to a blend of 187B and 187C; distal 33% of the petal, close to 71D; towards the base, close to a blend of 76A and 76B and at the base, close to 145C; venation, similar to lamina colors; color does not change with subsequent development. Fully developed, lower surface: Close to 76C; distal 33% of the petal, close to 71D; towards the base, close to 144C; venation, similar to lamina colors; color does not change with subsequent development.

*Petaloids.*—Quantity and arrangement: About four petaloids arranged in a single whorl. Length: About 2.9 cm; ranging from 2.7 cm to 3 cm. Width: About 1.4 cm; ranging from 1.2 cm to 1.6 cm. Shape: Spatulate. Apex: Praemorse to narrowly emarginate. Base: Narrowly cuneate to acuminate. Margin: Distally, irregularly and finely dentate; proximally, entire; not undulate. Texture and luster, upper surface: Smooth, glabrous; velvety; matte. Texture and luster, lower surface: Smooth, glabrous; velvety; slightly glossy. Color: When opening, upper surface: Close to a blend of 187C and 187D; distal 50% of the petal, close to NN78A; towards the base, close to NN155D and at the base, close to 149D; occasional axial line, close to 76C. When opening, lower surface: Close to 71C; towards the base, close to N74C and at the base, close to 145B. Fully developed, upper surface: Close to a blend of 187B and 187C; distal 33% of the petal, close to 71D; towards the base, close to a blend of 76A and 76B and at the base, close to 145C; occasional axial line, close to 76C; venation, similar to lamina colors; color does not change with subsequent development. Fully developed, lower surface: Close to 76C; distal 33% of the petal, close to 71D; towards the base, close to 144C; venation, similar to lamina colors; color does not change with subsequent development.

*Sepals.*—Quantity and arrangement: Five sepals arranged in a single whorl; proximal 80% of the sepal is fused into a campanulate-shaped calyx. Calyx length: About 1.9 cm. Calyx diameter: About 5 mm. Sepal length: About 1.9 cm. Sepal width, at base of "free" portion: About 3 mm. Shape: Narrowly oblong. Apex: Broadly acute. Margin: Entire. Texture and luster, upper and lower surfaces: Smooth, glabrous; slightly glossy. Color: When opening, upper surface: Close to 144A; towards the base, close to 144B; apical margin, occasionally tinged with close to 73B. When opening, lower surface: Close to 144A; apical margin, occasionally tinged with close to 73C. Fully opened, upper surface: Close to 143A; towards the base, close to 144A; apical margin, close to 187A. Fully opened, lower surface: Close to 144A; apical margin, close to N78B.

*Peduncles.*—Length: About 2 cm. Diameter: About 1 mm. Strength: Moderately strong. Aspect: About 25° to 45° from the stem axis. Texture and luster: Smooth, glabrous; moderately glossy overlain with a thin waxy layer which is matte. Color: Close to 144A; waxy layer, close to N155A.

*Pedicels (for flowers in pairs).*—Length flowers: About 1 mm. Diameter: About 1 mm. Strength: Moderately strong. Aspect: About 10° from the peduncle axis. Texture and luster: Smooth, glabrous; moderately glossy overlain with a thin waxy layer which is matte. Color: Close to 144A; waxy layer, close to N155A.

*Reproductive organs.*—Stamens: Quantity: Typically eight. Filament length: About 1.1 cm. Filament color: Close to 145D. Anther size: About 1 mm by 1.5 mm. Anther shape: Irregularly oblong, partially transformed into petaloids. Anther color: Close to 162C. Pollen: None observed. Pistils: Quantity: Typically two per flower. Pistil length: About 1.5 cm. Stigma diameter: About 1 mm. Stigma shape: Pointed, curved. Stigma color: Close to 77B. Style length: About 1.8 cm. Style color: Close to N155D; distally, close to 76A. Ovary color: Close to 150D; distally, close to N144A. Fruits and seeds: To date, fruit and seed development have not been observed on plants of the new *Dianthus*.

Pathogen & pest resistance: To date, plants of the new *Dianthus* have not been observed to be resistant to pathogens and pests common to *Dianthus* plants.

Garden performance: Plants of the new *Dianthus* have been observed to tolerate rain, wind, temperatures ranging from −20° C. to about 35° C. and to be suitable for USDA Hardiness Zones 5 to 9.

It is claimed:

1. A new and distinct *Dianthus* plant named 'Hilpicperf' as herein illustrated and described.

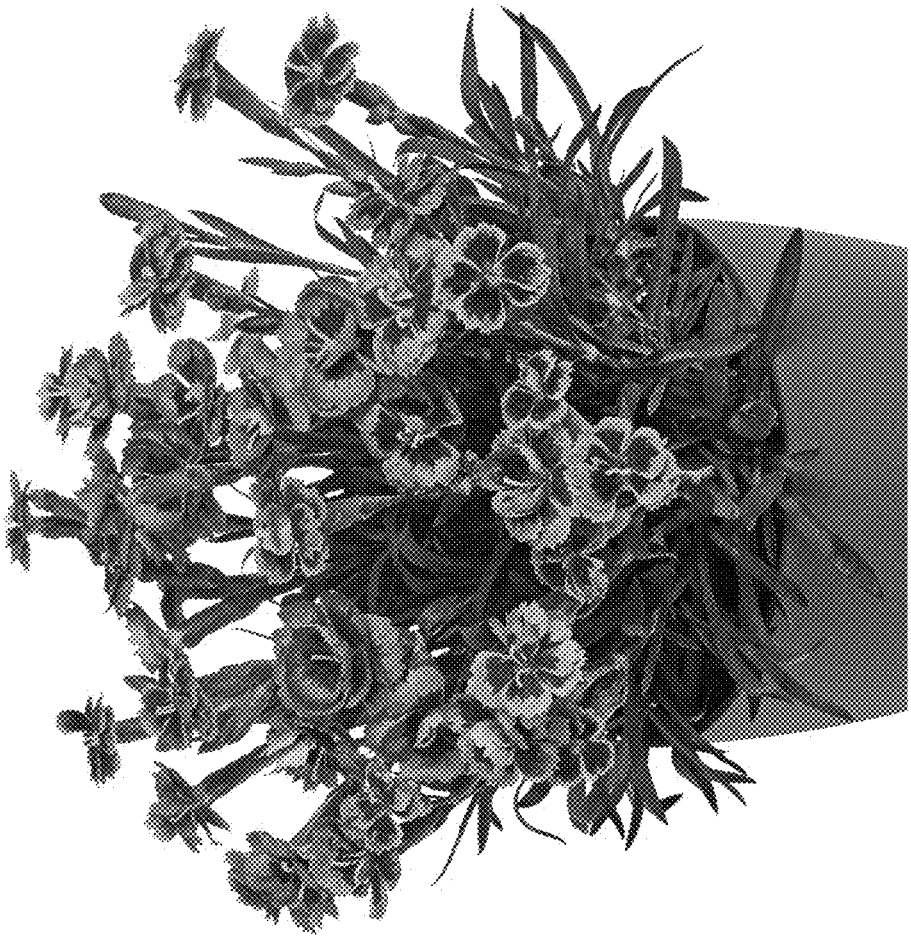

* * * * *